US012059201B2

(12) United States Patent
Iaizzo et al.

(10) Patent No.: US 12,059,201 B2
(45) Date of Patent: *Aug. 13, 2024

(54) METHOD FOR CLOSURE AND ABLATION OF ATRIAL APPENDAGE

(71) Applicant: Medtronic, Inc., Minneapolis, MN (US)

(72) Inventors: Paul A. Iaizzo, White Bear, MN (US); Ryan P. Goff, Costa Mesa, CA (US)

(73) Assignee: Medtronic, Inc., Minneapolis, MN (US)

( * ) Notice: Subject to any disclaimer, the term of this patent is extended or adjusted under 35 U.S.C. 154(b) by 855 days.

This patent is subject to a terminal disclaimer.

(21) Appl. No.: 17/000,434

(22) Filed: Aug. 24, 2020

(65) Prior Publication Data

US 2020/0383726 A1     Dec. 10, 2020

Related U.S. Application Data

(62) Division of application No. 14/879,399, filed on Oct. 9, 2015, now Pat. No. 10,786,302.

(51) Int. Cl.
*A61B 18/14*     (2006.01)
*A61B 17/12*     (2006.01)
(Continued)

(52) U.S. Cl.
CPC .... *A61B 18/1492* (2013.01); *A61B 17/12013* (2013.01); *A61B 18/02* (2013.01);
(Continued)

(58) Field of Classification Search
CPC ...... A61B 18/1492; A61B 2017/00243; A61B 2017/00358; A61B 2018/00351; A61B 2018/0212; A61B 2018/141
See application file for complete search history.

(56) References Cited

U.S. PATENT DOCUMENTS 5,814,052 A * 9/1998 Nakao ............... A61B 18/1492
                                                   606/115
6,488,689 B1   12/2002 Kaplan et al.
(Continued)

FOREIGN PATENT DOCUMENTS

EP       2019633 A1   2/2009
WO   2005046453 A2   5/2005

OTHER PUBLICATIONS

Leonid Sternik, MD et al., Box lesion in the open left atrium for surgical ablation of atrial fibrillation, The Journal of Thoracic and Cardiovascular Surgery, Mar. 2014, 4 pages.
(Continued)

*Primary Examiner* — Michael F Peffley
*Assistant Examiner* — Samantha M Good
(74) *Attorney, Agent, or Firm* — Michael Best & Friedrich LLP

(57) ABSTRACT

A device, system, and method for ligating the left atrial appendage without creating pro-arrhythmic tissue. The device may generally include a snare including a thermally transmissive distal portion and a suture including a distal portion, both distal portions having a lasso-shaped configuration that may be positioned proximate the base of the left atrial appendage. Once the distal portions of the snare and the suture are tightened around the base of the left atrial appendage, the thermally transmissive distal portion of the snare may be activated to create an ablation lesion in adjacent left atrial appendage tissue. The lesion may be created with radiofrequency energy or through cryoablation by the circulation of refrigerant within the thermally transmissive distal portion of the snare.

18 Claims, 12 Drawing Sheets

(51) Int. Cl.
*A61B 18/02* (2006.01)
*A61B 17/00* (2006.01)
*A61B 18/00* (2006.01)

(52) U.S. Cl.
CPC ............... *A61B 2017/00243* (2013.01); *A61B 2017/00358* (2013.01); *A61B 2018/00351* (2013.01); *A61B 2018/00577* (2013.01); *A61B 2018/0212* (2013.01); *A61B 2018/0225* (2013.01); *A61B 2018/0262* (2013.01); *A61B 2018/0293* (2013.01); *A61B 2018/141* (2013.01); *A61B 2217/007* (2013.01); *A61B 2218/002* (2013.01)

(56) References Cited

U.S. PATENT DOCUMENTS

| | | |
|---|---|---|
| 6,595,989 B1 | 7/2003 | Schaer |
| 6,905,498 B2 | 6/2005 | Hooven |
| 8,409,219 B2 | 4/2013 | Kelley et al. |
| 8,469,950 B2 | 6/2013 | Stein et al. |
| 10,786,302 B2* | 9/2020 | Iaizzo .................... A61B 18/02 |
| 2005/0085883 A1 | 4/2005 | Ollivier et al. |
| 2005/0137591 A1* | 6/2005 | Barry ................. A61B 18/1482 606/45 |
| 2005/0137669 A1 | 6/2005 | Krishnan et al. |
| 2006/0041300 A1 | 2/2006 | Zhang et al. |
| 2008/0009843 A1 | 1/2008 | de la Torre |
| 2008/0033241 A1 | 2/2008 | Peh et al. |
| 2011/0282250 A1 | 11/2011 | Fung et al. |
| 2012/0330351 A1 | 12/2012 | Friedman et al. |
| 2014/0303721 A1 | 10/2014 | Fung et al. |

OTHER PUBLICATIONS

International Search Report and Written Opinion dated Dec. 7, 2016, for corresponding International Application No. PCT/US2016/053752; International Filing Date: Sep. 26, 2016 consisting of 14-pages.

* cited by examiner

METHOD FOR CLOSURE AND ABLATION OF ATRIAL APPENDAGE

CROSS-REFERENCE TO RELATED APPLICATION

This application is a divisional to U.S. application Ser. No. 14/879,399, filed Oct. 9, 2015, now issued as U.S. Pat. No. 10,786,302, the entirety of which is incorporated herein by reference.

STATEMENT REGARDING FEDERALLY SPONSORED RESEARCH OR DEVELOPMENT n/a

TECHNICAL FIELD

The present invention relates to a device, system, and method for ligating the left atrial appendage without creating pro-arrhythmic tissue. Specifically, the present invention relates to a device, system, and method for ligating the left atrial appendage and for ablating a portion of the left atrial appendage that is proximate the ligation location.

BACKGROUND

Patients with atrial fibrillation, particularly patients with non-valvular atrial fibrillation, are five times more likely of having a stroke than patients without atrial fibrillation. This increased risk is believed to original from the left atrial appendage (LAA), a muscular pouch within the pericardium and connected to the left atrium of the heart. Blood may pool within the LAA, and this pooled blood may have a tendency to form clots, which can dislodge from the LAA and form emboli. In fact, it is believed that over 90% of clots form in the LAA.

Consequently, removing or excluding (occluding) the LAA is believed to reduce the risk of stroke, especially in patients with atrial fibrillation. LAA occlusion (which may also be referred to herein as exclusion or ligation) may be accomplished by using an endocardially placed occlusion device, for example, a Transcatheter Patch (Custom Medical devices, Athens, Greece), the PLAATO™ device (ev3, Sunnyvale, CA), or WATCHMAN® device (Boston Scientific, Marlborough, MA). Alternatively, LAA occlusion may at least partially involve an epicardially placed occlusion device. There are two commonly used methods of performing LAA occlusion: one method uses endocardial and epicardial magnetized guides that stabilize the LAA by the magnetic force between the two guides through the LAA tissue. Once the LAA is stabilized, a snare is passed over the LAA and used to ligate or suture the LAA (for example, the LARIAT™ (SentreHeart, Inc., Redwood City, CA). The other method involves a purely epicardial approach in which, via subxiphoid access, the LAA is identified and inserted into a clamp device (for example, the ATRICLIP® (AtriCure, Inc., West Chester, OH)). The clamp then remains implanted within the patient. All of these methods are meant to isolate the LAA and prevent blood clots from exiting the LAA and traveling as emboli through the bloodstream.

Although these methods may be effective in ligating the LAA, the resulting damage to the cardiac tissue, including the LAA, may actually create temporary or permanent pro-arrhythmic tissue. Heterogeneous tissue has been shown to cause or maintain arrhythmias. When a ligating device such as those mentioned above closes on the LAA, the tissue may begin to die. Hypoxia of tissue alone may cause a wide variety of tissue abnormalities, and the zone of dead tissue around the closure device may also be non-uniform with strange morphology. For example, the dead tissue may have a jagged lesion margin.

It is therefore desirable to provide a method, system, and device for performing LAA occlusion/ligation that creates a more uniform boundary between dead tissue and living tissue and which is less likely to create pro-arrhythmic tissue.

SUMMARY

The present invention advantageously provides a device, system, and method for ligating the left atrial appendage without creating pro-arrhythmic tissue. In general, a snare having a thermally transmissive distal portion may be used to create a lesion within left atrial appendage tissue that is proximate a suture used to ligate the left atrial appendage. The combination of ablation and ligation may avoid undesired secondary effects that may occur when using ligation alone. A device for ligating a left atrial appendage may include a first elongate body including a proximal portion and a thermally transmissive distal portion and a second elongate body having a proximal portion and a distal portion, the distal portion of the second elongate body being releasably engageable with the proximal portion of the second elongate body. The thermally transmissive distal portion of the first elongate body may have a lasso-shaped configuration, which may have an adjustable diameter. Likewise, the distal portion of the second elongate body may have a lasso-shaped configuration, which may have an adjustable diameter. The distal portion of the first elongate body may include a first slidable element that is slidably engaged with a portion of the first elongate body and the distal portion of the second elongate body may include a second slidable element that is slidably engaged with a portion of the second elongate body. The first slidable element may also be slidably engaged with a portion of the second elongate body and the second slidable element may also be slidably engaged with a portion of the first elongate body. The thermally transmissive distal portion of the first elongate body may be configured to transmit radiofrequency energy. For example, at least the thermally transmissive distal portion of the first elongate body may be composed of an electrically conductive material. Additionally or alternatively, the first elongate body may define a fluid lumen therein, the fluid lumen being configured to be in fluid communication with a source of refrigerant. In this manner, the distal portion of the first elongate body may be configured to reach a temperature that is sufficiently low enough to ablate adjacent tissue through cryoablation.

A system for ligating a left atrial appendage may include a ligation device including: a snare having an elongate body having a proximal portion and a thermally transmissive distal portion, the thermally transmissive distal portion having a lasso-shaped configuration defining a first diameter; a suture having an elongate body having a proximal portion and a distal portion, the distal portion having a lasso-shaped configuration defining a second diameter, and a console in at least one of electrical communication and fluid communication with the thermally transmissive distal portion of the snare. Each of the first diameter and the second diameter may be independently adjustable within a range of a plurality of diameters. For example, the range of the plurality of diameters may include a diameter sized to allow the left atrial appendage to pass therethrough and a diameter sized to ligate the left atrial appendage. The console may include a radiofrequency energy generator, the thermally transmissive distal portion of the snare being configured to transmit radiofrequency energy from the radiofrequency energy generator to the left atrial appendage. Additionally or alternatively, the console may include a refrigerant source, the thermally transmissive distal portion defining a fluid lumen therein that is in fluid communication with the refrigerant source.

A method of ligating a left atrial appendage of a patient may include: adjusting a diameter of a lasso-shaped, thermally transmissive distal portion of a first medical device to a first diameter such that the distal portion of the first medical device is in contact with the left atrial appendage; adjusting a diameter of a lasso-shaped distal portion of a second medical device to a second diameter such that the distal portion of the second medical device is in contact with the left atrial appendage, the second diameter being approximately the same as the first diameter; and ablating a portion of the left atrial appendage proximate the distal portion of the second medical device with the distal portion of the first medical device. The method may further include adjusting the diameter of the distal portion of the second medical device such that the distal portion of the second medical device. The method may further include removing the first medical device from the patient.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
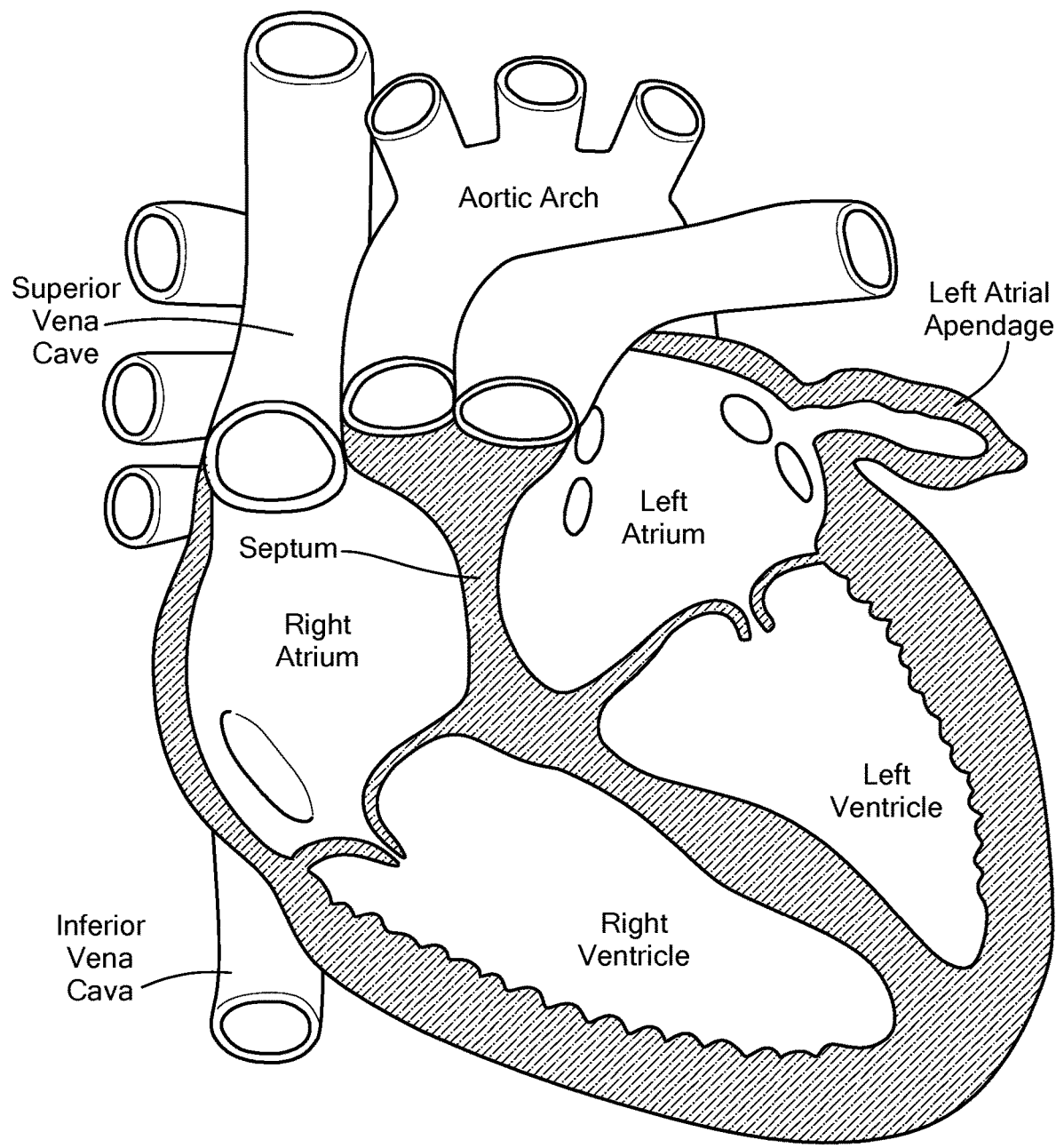
FIG. 1 shows a heart, including a left atrial appendage (LAA)

Referring now to FIG. 1, a human heart is shown. The heart includes a left atrial appendage (LAA) (also sometimes referred to as the left auricular appendix, auricular, or left auricle). The LAA is a small, muscular pouch within the pericardium that opens into the left atrium. As previously discussed, most emboli are believed to originate from the LAA, and those with atrial fibrillation are at the most risk of having a stroke. Therefore, it may be desirable to exclude, or isolate, the LAA from the patient's bloodstream to reduce the risk of emboli escaping from the LAA. Closing the LAA using an endocardial or epicardial device may be referred to as ligating the LAA.

Figure 2:
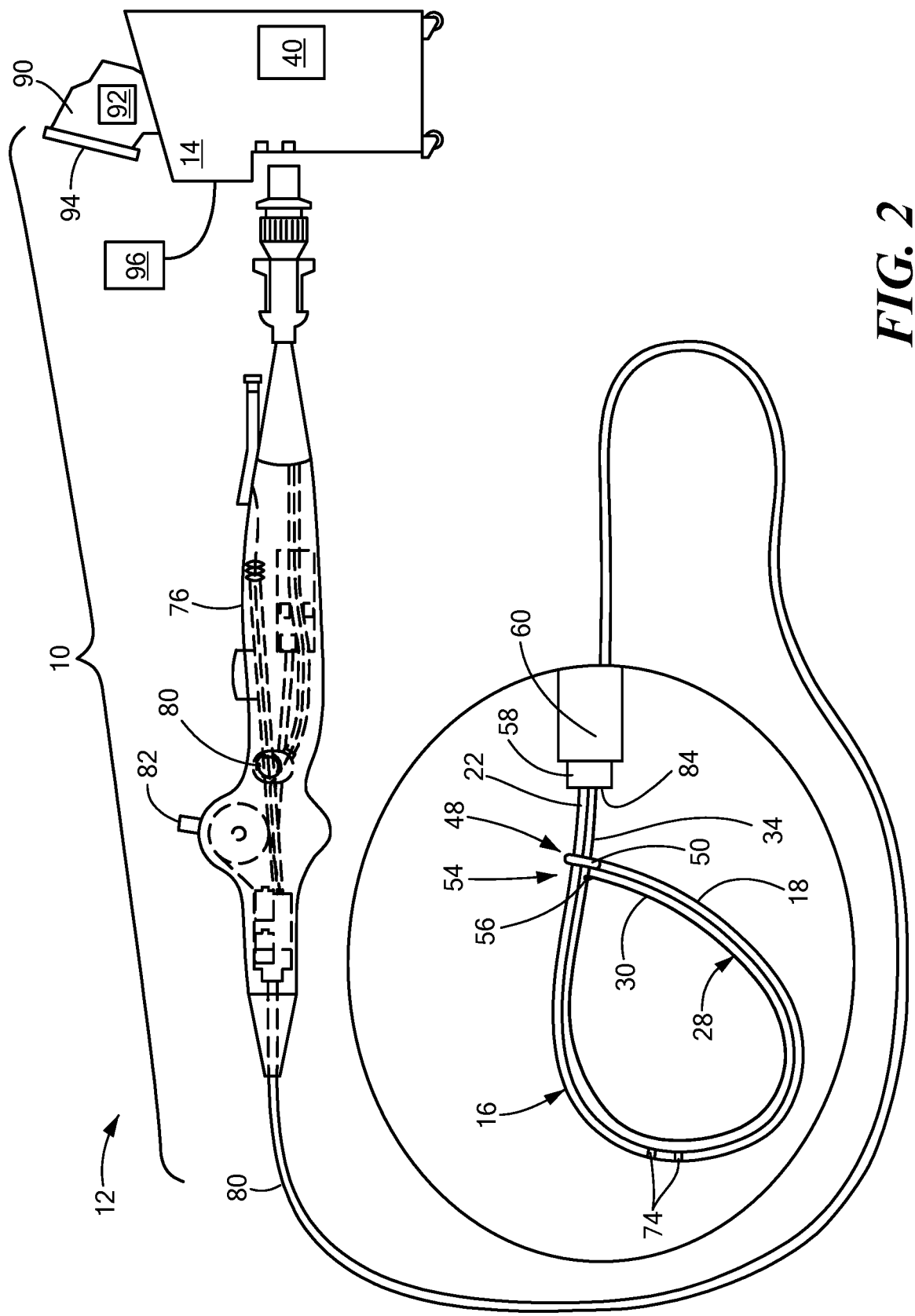
FIG. 2 shows an exemplary system that includes a first embodiment of a ligation device.

Referring now to FIG. 2, an exemplary system that includes a first embodiment of a ligation device is shown. The system 10 may generally include a ligation device 12 in fluid communication with a console 14. The device 12 may include a snare 16 including distal portion 18, a proximal portion (not shown), and an elongate body 22 therebetween. The device 12 may also include a suture 28 including a distal portion 30, a proximal portion (not shown), and an elongate body 34 therebetween. The distal portion 30 of the suture 28 optionally may be detachedly coupled to the distal portion 18 of the snare 16, and the proximal portion of the snare 16 may be in electrical communication with a radiofrequency generator 40. Further, each of the snare 16 and suture 28 may include a constant or substantially constant diameter and circumference from the proximal portion to the distal portion 18, 30. The snare 16 and the suture 28 may have the same or different diameters and circumferences. As a non-limiting example, the snare 16 and the suture 28 may each be composed of a wire or filament of material. At least the distal portion 18 of the snare 16 may be electrically conductive (for example, the distal portion 18 may be composed of a metal wire), whereas the suture 28 may be non-conductive (for example, the distal portion 30 may be composed of a plastic or non-conductive polymer).

The distal portion 18 of the snare 16 and the distal portion 30 of the suture 28 may each have a lasso configuration (that is, a closed loop or circular configuration). For example, the distalmost end 48 of the snare 16 may include a slidable element 50 that is movable along a more proximal portion of the snare 16, such that the lasso shape of the snare 16 may be reduced or enlarged. Likewise, the distalmost end 54 of the suture 28 may likewise include a slidable element 56 that is movable along a more proximal portion of the suture 28, such that the lasso shape of the suture 28 may be reduced or enlarged. As a non-limiting example, the slidable elements 50, 56 may be a loop formed by the snare 16 and suture 28, respectively, a ring, or other element defining an opening through which the elongate body of the snare 16 and suture 28, respectively, may pass. The opening of the slidable element 50 may be sized such that a more proximal portion of the snare 16 may pass without impediment. Alternatively, the opening of the slidable element 50 may be sized such that friction between the opening and the snare 16 maintains the size of the lasso created by the user. Likewise, the opening of the slidable element 56 may be sized such that a more proximal portion of the suture 28 may pass without impediment. Alternatively, the opening of the slidable element 56 may be sized such that friction between the opening and the suture 28 maintains the size of the lasso created by the user.

The device 12 may further include a first sheath 58 that retains at least a portion of the snare elongate body 22 and the suture elongate body 34 during a procedure to ensure the snare 16 and the suture 28 are kept together. The device 12 may further include a second sheath 60 that surrounds the first sheath 58. Each of the first sheath 58 and second sheath 60 may be slidable (that is, longitudinally movable) relative to each other and to the snare elongate body 22 and the suture elongate body 34. As is described in more detail below, the first sheath 58 may be advanced against the slidable elements 50, 56 to urge the slidable elements 50, 56 to slide along the snare 16 and the suture 28, respectively, thereby tightening (reducing the diameter of) the lasso portions.

Figure 4A:
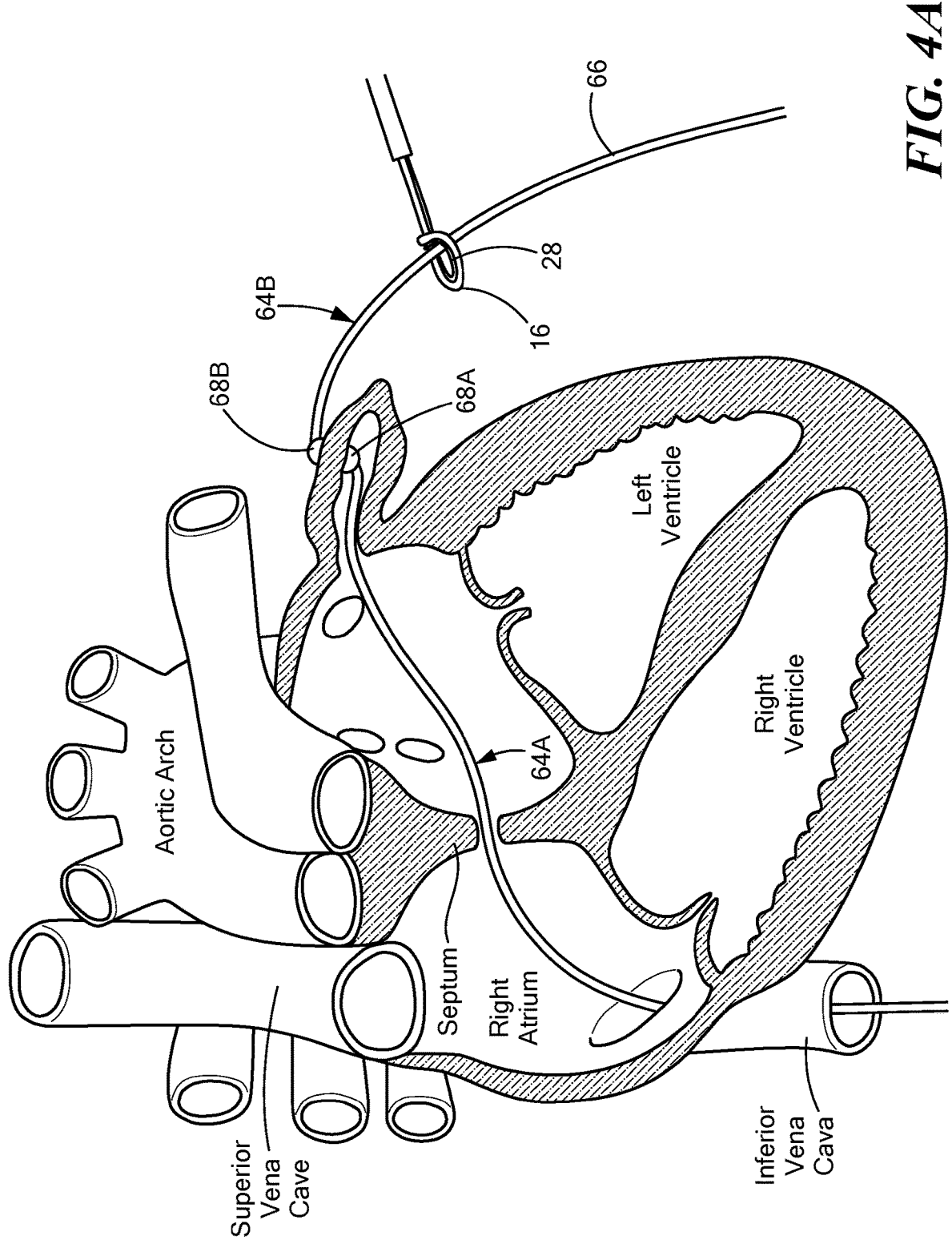
FIG. 4A shows a ligation device being advanced over the elongate body of a first anchoring device.
Figure 4B:
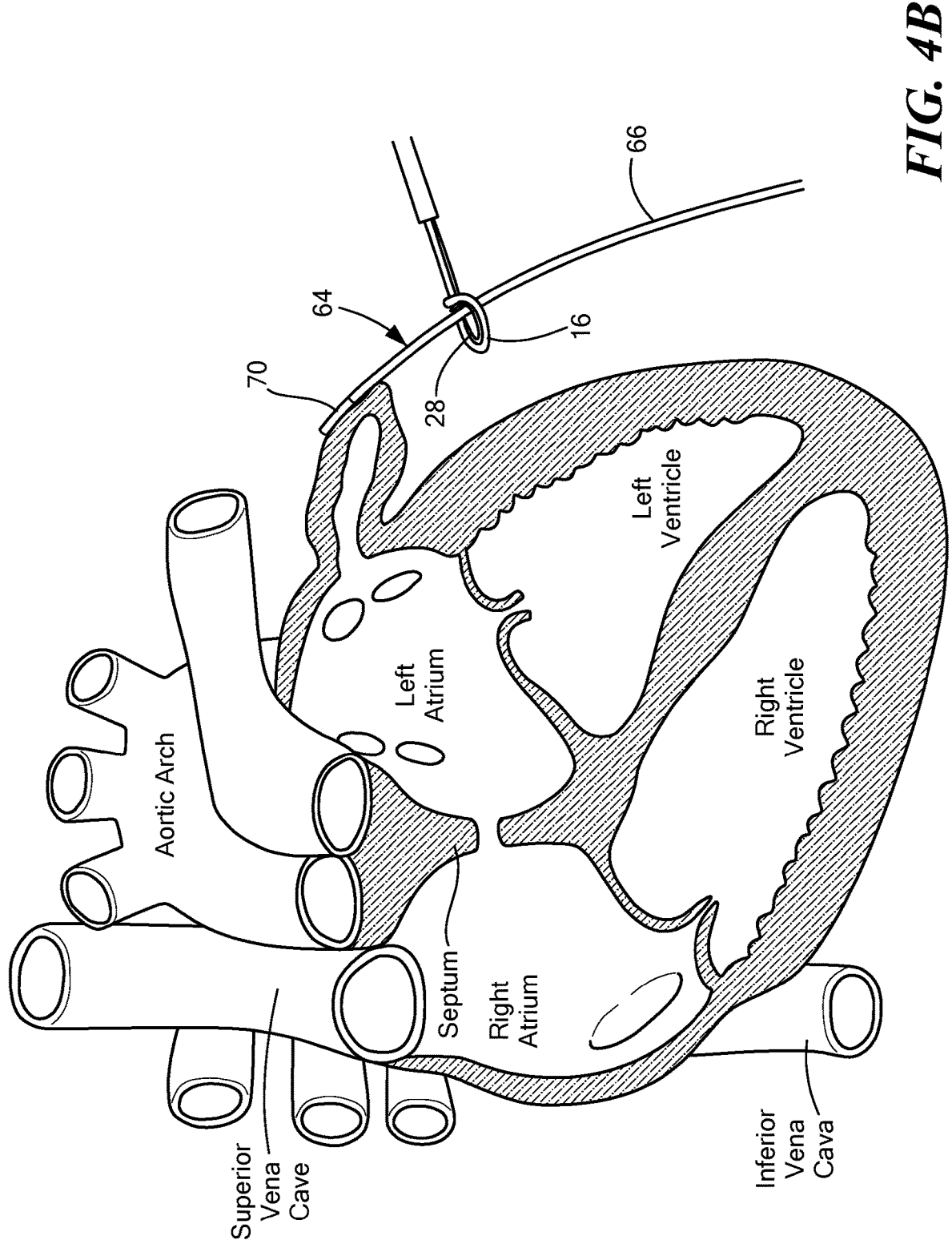
FIG. 4B shows a ligation device being advanced over the elongate body of a second anchoring device.

The snare 16 and the suture 28 optionally may be detachedly coupled to each other so the distal portions 18, 30 stay near each other for positioning relative to the LAA. For example, the snare 16 may include a clip, hook, adhesive coating or material, or other element for retaining at least a portion of the suture 28. The lasso-shaped distal portion 18, 30 of the snare 16 and the suture 28, respectively, may be passed over the elongate body of an anchoring device 64 that is anchored to the LAA. As a non-limiting example, the distal portions 18, 30 may be passed over the elongate body 66 of an anchoring device 64 that includes an endocardial first component 64A that includes, for example, a first magnet 68A, and an epicardial second component 64B that includes a second magnet 68B. The first 64A and second 64B components may be anchored together through the LAA tissue, and in that manner anchored to the LAA, by the magnetic attraction between the first 68A and second 68B magnets (as shown in FIG. 4A). For example, the magnets 68A, 68B may be electromagnets for easy release from the LAA tissue once the suture 28 is in place. Alternatively, the lasso-shaped distal portions 18, 30 may be advanced over the elongate body 66 of an epicardial anchoring device that includes a cooled distal tip 70. The cooled distal tip 70 may be reduced to a temperature low enough to cause cryoadhesion between the anchoring device 64 and the LAA, thus anchoring the anchoring device 64 (as shown in FIG. 4B). Passing the distal portions 18, 30 of the snare 16 and the suture 28 over the epicardial second component 64B of the anchoring device 64 may facilitate proper positioning of the distal portions 18, 30 about the base of the LAA. Further, the suture 28 may include a point of detachment for separating the lasso portion (at least a portion of the distal portion 30 of the suture 28) from the rest of the suture elongate body 34. For example, the suture 28 may include an area proximate the lasso portion when fully tightened that is manufactured to be weaker than the rest of the suture 28 such that sufficient force exerted on the suture elongate body 34 may break the suture 28, thereby separating the lasso portion so it can be left around the LAA within the patient's body when the procedure is finished. Additionally or alternatively, the device 12 may include a cutting element 72 within the first sheath 58 that severs the lasso portion of the suture 28. As a non-limiting embodiment, the cutting element 72 may include a small blade that is actuated at the handle by, for example, a slider or knob. When actuated, the blade may cut through the suture 28 to separate the lasso portion from the rest of the suture 28.

Optionally, the device 12 may include one or more electrodes 74 for monitoring an electrical signal from the LAA to obtain information such as confirmation of proper placement of the device onto LAA tissue, tissue contact, and for visualization with a navigation system, such as NAVX™ (St. Jude Medical, Inc., St. Paul, MN). The one or more electrodes 74 may also be used to determine whether ligation of the LAA has occurred. For example, the one or more electrodes 74 may be located on the distal portion 18 of the snare 16. When the snare is tightened around the LAA, the one or more electrodes 74 may detect very few or no electrical signals from the LAA tissue. Conversely, if the one or more electrodes 74 detect a normal amount of electrical signals, the system 10 may alert the operator that the LAA is not ligated.

The device 12 may further include a handle 76 that is operably coupled to the snare proximal portion the suture proximal portion 32, and a proximal portion 78 of the first sheath 58. The handle 76 may also be coupled to a proximal portion 80 of the second sheath 60. Alternatively, each of the snare 16 and the suture 28 may each include a handle (not shown). In such a configuration, the snare 16 and suture 28 together may be considered to be the ligation device 12. As shown in FIG. 2, the handle 76 may include one or more knobs, wheels, buttons, or other actuators for navigation and manipulation of the device 12. For example, the handle 76 may include a knob, wheel, or other actuator 82 that is in mechanical communication with the proximal portion 78 of the first sheath 58. Actuation of the knob 82 may advance or retract the first sheath over the snare elongate body 22 and the suture elongate body 34 in order to adjust the size of the lasso portion of the snare 16 and the lasso portion of the suture 28. For example, the knob 82 may be actuated to advance the distal portion 84 of the first sheath 58 against the slidable elements 50, 56 to urge the slidable elements 50, 56 along the snare 16 and the suture 28, respectively, thereby tightening (reducing the diameter of) the lasso portions. Further, the handle 76 may include a rotary mechanism 86 within that winds or otherwise collects any slack at the distal portion of at least the suture 28, and optionally the snare 16, in order to put tension on at least the suture 28. The first sheath 58 and the rotary mechanism 86 may together ensure that the lasso portion of the suture 28 can not only be tightened about the LAA, but also that it will remain tightened. As mentioned above, the handle 76 may also include a cutting element 72 that severs the lasso portion of the suture 28 from the rest of the suture 28.

The console 14 may include a radiofrequency energy generator 40 in electrical communication with the snare 16 and, optionally, the one or more electrodes 74. It will be understood that the radiofrequency energy generator 40 may be located external to the console 14; however, for simplicity, any element that is not included in the ligation device may be referred to as being a part of the console 14. Additionally or alternatively, the system may also be configured to deliver irreversible electroporation energy, high intensity focused ultrasound, laser energy, microwave energy, or combinations thereof, and may also be configured for use in cryoablation procedures. The console 14 may also include one or more computers 90 having one or more processors 92 that are programmed or programmable to receive and interpret data from the one or more electrodes 74 and/or one or other sensors throughout the system (for example, temperature or pressure sensors) using one or more algorithms. The one or more processors 92 may also be programmed or programmable to control transmission of energy from the radiofrequency energy generator 40 to the snare 16. Although not shown, the ligation device 12 may further include one or more temperature sensors and the one or more processors 92 may also process received data using one or more algorithms to, for example, determine the temperature of the snare 16 and/or adjacent tissue. The console 14 may also include one or more displays 94 and user input devices 96 such as buttons, knobs, scroll wheels, keyboards, mice, touchscreens, or the like. The console 14 may communicate received and/or processed data to the operator, such as through a display screen 94 and/or one or more audible or visual alerts.

Figure 3A:
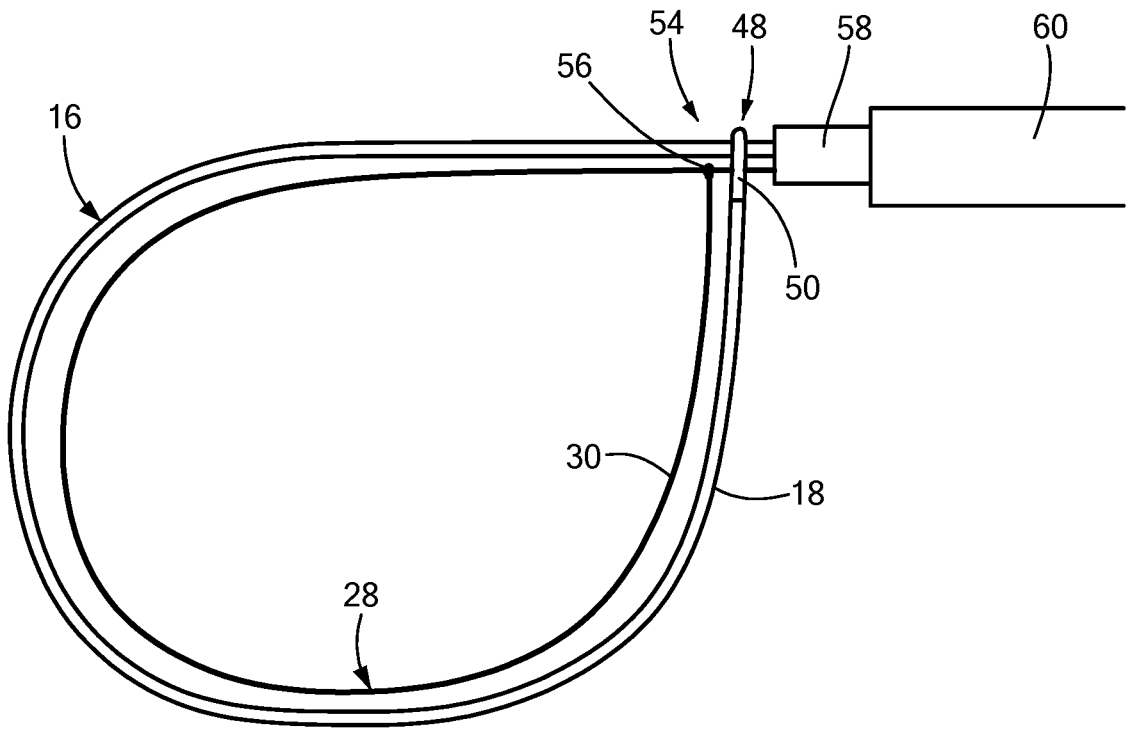
FIG. 3A shows a distal portion of the ligation device in an expanded lasso configuration.
Figure 3B:
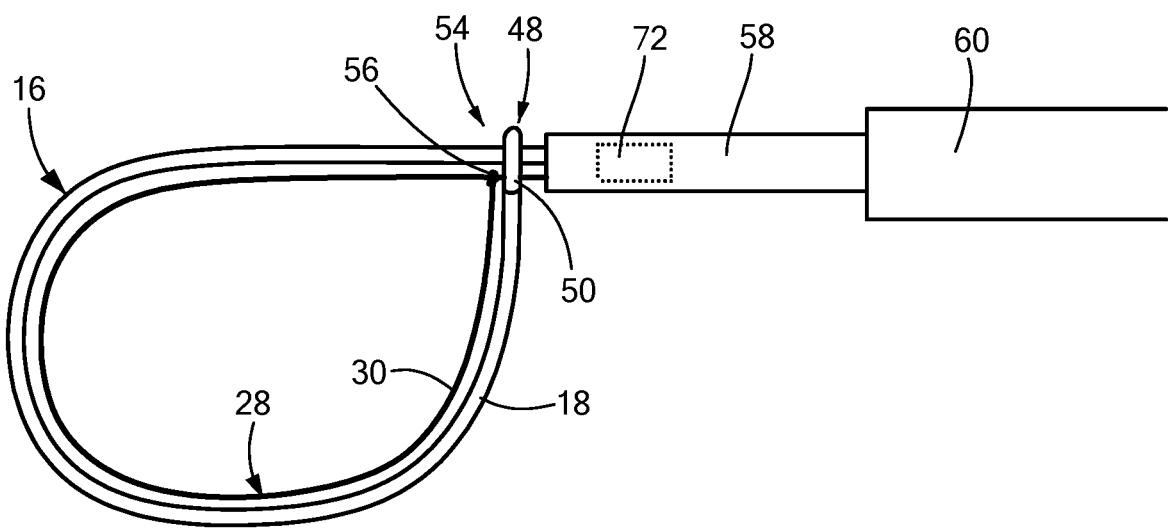
FIG. 3B shows the distal portion of the ligation device in a reduced lasso configuration.

Referring to FIGS. 3A and 3B, the first embodiment of the ligation device is shown in more detail. As shown and described in FIG. 2, the snare 16 and the suture 28 may each have a lasso configuration that is transitionable between an expanded configuration having a first diameter (for example, as shown in FIG. 3A) and a reduced configuration having a second diameter (for example, as shown in FIG. 3B). The expanded configuration may be used when positioning the distal portions 18, 30 of the snare 16 and suture 28, respectively, around the LAA. Once in position, the lasso of each of the distal portions 18, 30 may be reduced to tighten around the LAA. The distal portions 18, 30 of each of the snare 16 and suture 28 may have approximately the same diameter, as shown in FIGS. 3A and 3B.

Figure 5A:
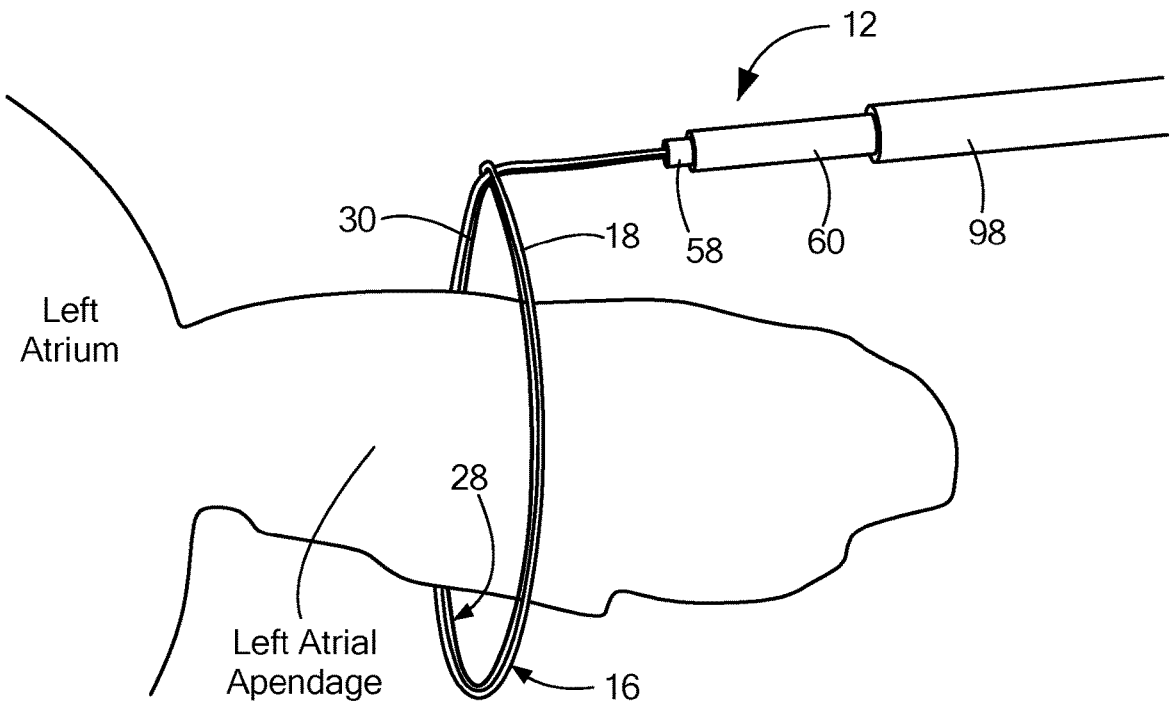
FIGS. 5A-5C show an exemplary method of ligating and ablating the LAA with radiofrequency energy using the ligation device shown in FIG. 2.
Figure 5B:
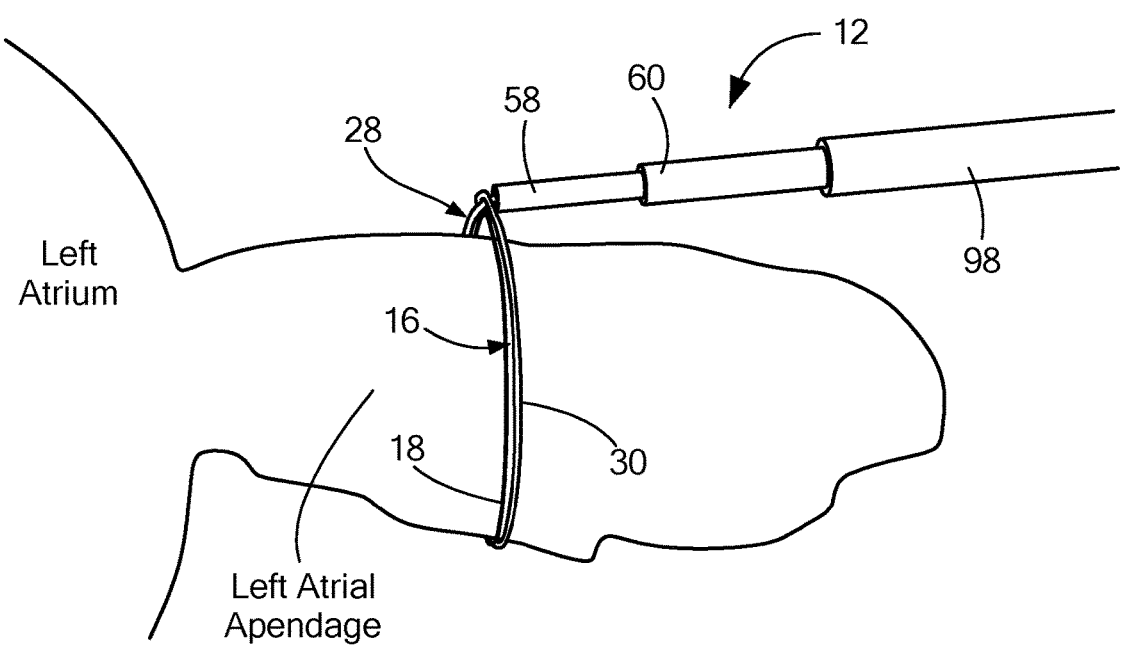
Figure 5C:
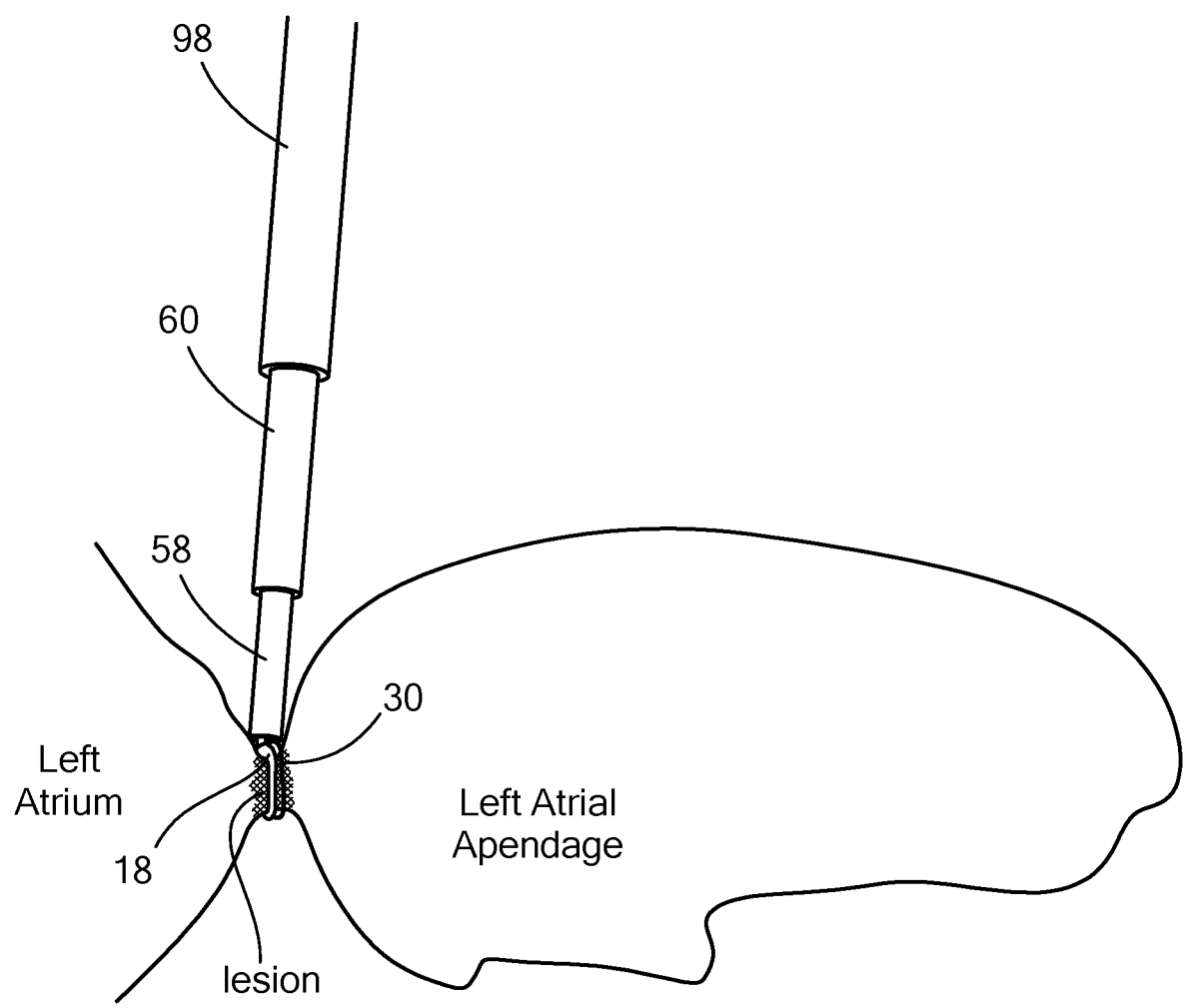

Referring now to FIGS. 5A-5C, a method of ligating and ablating the LAA using the ligation device of FIG. 2 is shown. The device 12 may be positioned in the pericardial space (that is, between the pericardium and the heart) proximate the LAA. For example, the device 12 may be advanced through a guide sheath 98 that is inserted into the patient's body before the ligation device 12. The device 12 may be inserted, within the guide sheath 98, via subxiphoid access into the pericardial space and positioned at the target treatment site proximate or in contact with the LAA, which is adjacent to the left atrium. Inserting the device 12 into the patient's body via subxiphoid access may be less invasive and traumatic to the patient than other means of access, such as a thoracotomy. Although the device 12 is not specifically shown within the guide sheath 98 for simplicity, it will be understood that the device 12 may remain within the guide sheath 98 until the device 12 is extended beyond the guide sheath98 at the target treatment site. During navigation through the patient's body and placement at the target treatment site, the distal portions 18, 30 of the snare 16 and suture 28 may be entirely or at least partially located within at least the first sheath 58. Once at the target treatment site, the snare 16 and the suture 28, or at least the distal portions 18, 30 thereof, may be advanced distally out of the guide sheath 98 and also out of the first 58 and second 60 sheaths of the device 12.

At least the distal portion 18 of the snare 16 may have ablative functionality to create a lesion on the LAA at the site of ligation. This lesion may reduce the likelihood of creating pro-arrhythmic tissue. All other portions of the snare elongate body 22 other than the distal portion 18 may be insulated or composed of a non-conductive material, whereas at least the distal portion 18 may be composed of an electrically conductive material, such as metal. Once the distal portions 18, 30 of the snare 16 and suture 28 are positioned such that they loosely surround the base of the LAA (for example, as shown in FIG. 5A), the distal portions 18, 30 may be partially tightened (that is, the lasso portion may have a somewhat reduced diameter) as shown and described above around the LAA (for example, as shown in FIG. 5B). The radiofrequency energy generator 40 then may be activated or instructed to transmit energy to the snare 16, which may deliver radiofrequency energy to the LAA. After this first energy delivery, the distal portions 18, 30 may be fully tightened about the base of the LAA (for example, as shown in FIG. 5C). After the distal portions 18, 30 are fully tightened, energy may be delivered again from the distal portion 18 of the snare 16 to the LAA.

The radiofrequency energy delivered by the snare 16 may be, for example, phased radiofrequency energy, pulsed field radiofrequency energy, or other delivery modalities. Although reference is made herein to the delivery of radiofrequency energy, it will be understood that other energy modalities additionally or alternatively may be used, such as microwave energy, ultrasound energy, electroporation energy, or the like. After ablation is complete, the distal portion 30 of the suture 28 uncoupled from the rest of the elongate body 34. Additionally, if any portion of the distal portion 30 of the suture 28 is coupled to a portion of the snare 16, the distal portion 30 of the suture 28 may also be uncoupled from the snare 16. For example, the distal portion 30 of the suture 28 may be coupled to the snare 16 using a light adhesive, such that the distal portion 30 of the suture 28 is easily separated from the snare 16 under tension. The distal portion 30 of the suture 28, which may be tightened around the base of the LAA, may now be left in place within the patient's body while the rest of the ligation device 12 is removed.

Figure 6:
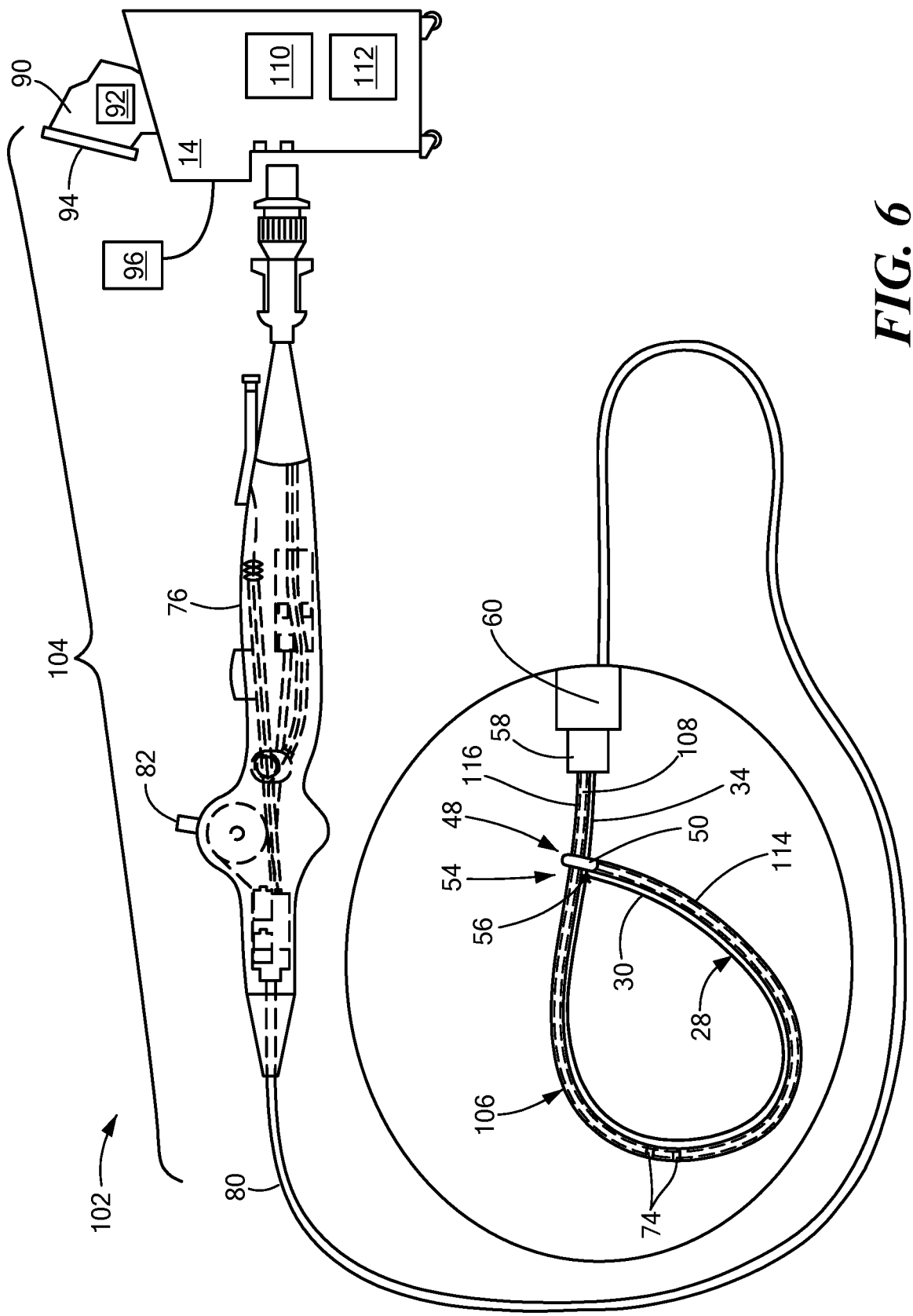
FIG. 6 shows an exemplary system that includes a second embodiment of a ligation device.

Referring now to FIG. 6, an exemplary system that includes a second embodiment of a ligation device is shown. The ligation device 102 and system 104 shown in FIG. 6 may be generally similar to the system 10 shown in FIG. 2 in structure, function, and delivery. However, unlike the system 10 shown in FIG. 2, the system 104 shown in FIG. 6 may be configured for cryogenic ablation of the LAA by the snare 106 rather than for radiofrequency ablation of the LAA by the snare 16. For example, the snare 106 may define a lumen 108 that is in fluid communication with a refrigerant source 110 and a refrigerant recovery reservoir 112 within the console 14. It will be understood that the refrigerant source 110 and the refrigerant recovery reservoir 112 may be located external to the console 14; however, for simplicity, any element that is not included in the ligation device may be referred to as being a part of the console 14. The console 14 may further include one or more valves or other fluid regulation devices to control the flow of refrigerant through the system 104.

Figure 7A:
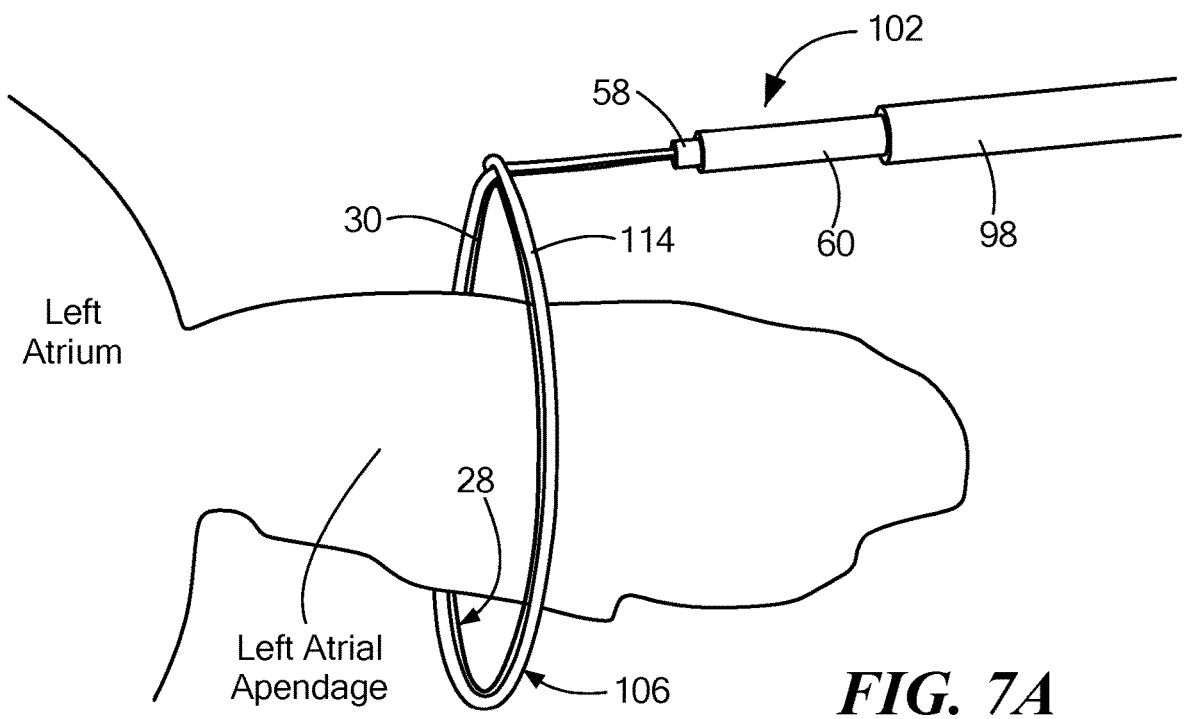
FIGS. 7A and 7B show an exemplary method of ligating and cryoablating the LAA using the ligation device shown in FIG. 6.
Figure 7B:
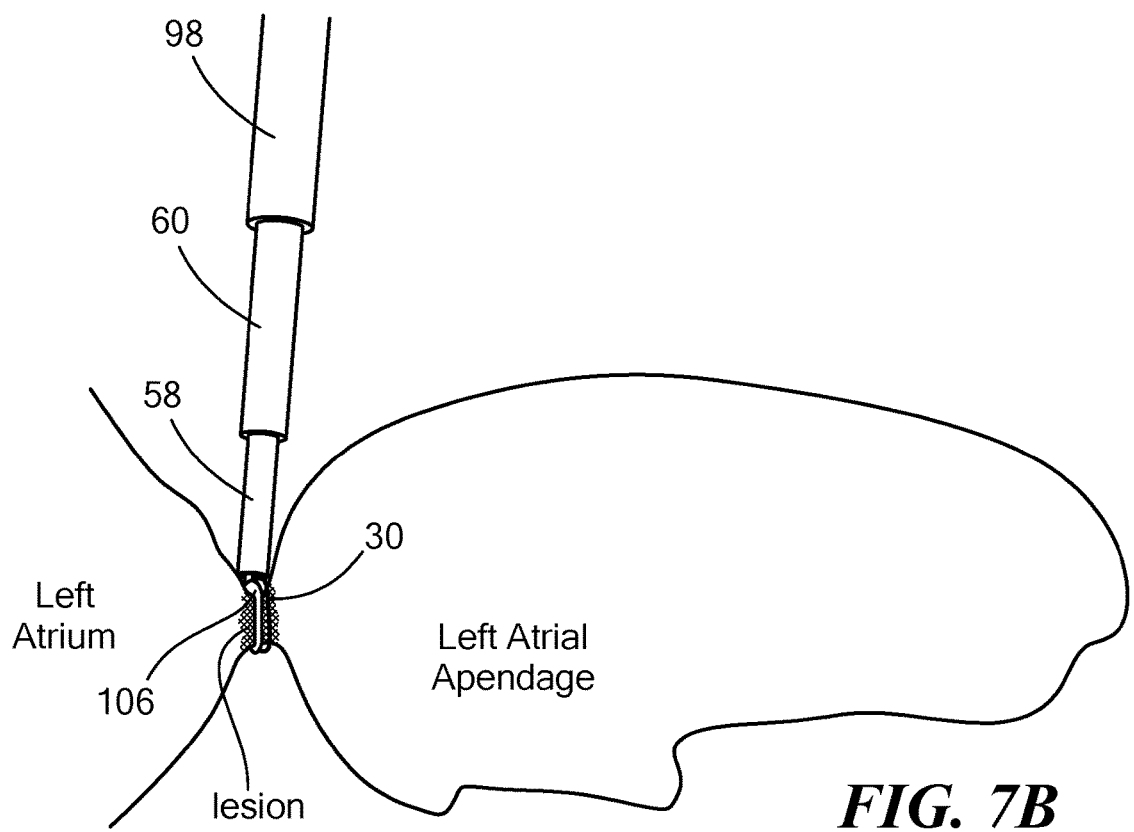

Referring now to FIGS. 7A and 7B, an exemplary method of ligating and cryoablating the LAA using the ligation device 102 is shown. The method is generally similar to the method using radiofrequency energy shown in FIGS. 5A-5C. The device 102 may be positioned in the pericardial space (that is, between the pericardium and the heart) proximate the LAA. For example, the device 102 may be advanced through a guide sheath 98 that is inserted into the patient's body before the ligation device 102. The device 102 may be inserted, within the guide sheath 98, via subxiphoid access into the pericardial space and positioned at the target treatment site proximate or in contact with the LAA, which is adjacent to the left atrium. Inserting the device 102 into the patient's body via subxiphoid access may be less invasive and traumatic to the patient than other means of access, such as a thoracotomy. Although the device 102 is not specifically shown within the guide sheath 98 for simplicity, it will be understood that the device 102 may remain within the guide sheath 98 until the device 102 is extended beyond the guide sheath 98 at the target treatment site. During navigation through the patient's body and placement at the target treatment site, the distal portions 114, 30 of the snare 106 and suture 28 may be entirely or at least partially located within at least the first sheath 58. Once at the target treatment site, the snare 106 and the suture 28, or at least the distal portions 114, 30 thereof, may be advanced distally out of the guide sheath 98 and also out of the first 58 and second 60 sheaths of the device 102.

At least the distal portion 114 of the snare 106 may have ablative functionality to create a lesion on the LAA at the site of ligation. This lesion may reduce the likelihood of creating pro-arrhythmic tissue. All other portions of the snare elongate body 116 other than the distal portion 114 may be insulated, whereas the distal portion 114 may be thermally transmissive. Once the distal portions 114, 30 of the snare 106 and suture 28 are positioned such that they loosely surround the base of the LAA (for example, as shown in FIG. 7A), the distal portions 114, 30 may be fully tightened around the LAA as shown and described above.

After the distal portions 114, 30 are fully tightened, refrigerant may be circulated through the distal portion 114 of the snare 106 to reduce the temperature of the distal portion 114 and create a cryoablation lesion in the adjacent LAA tissue.

Figure 8A:
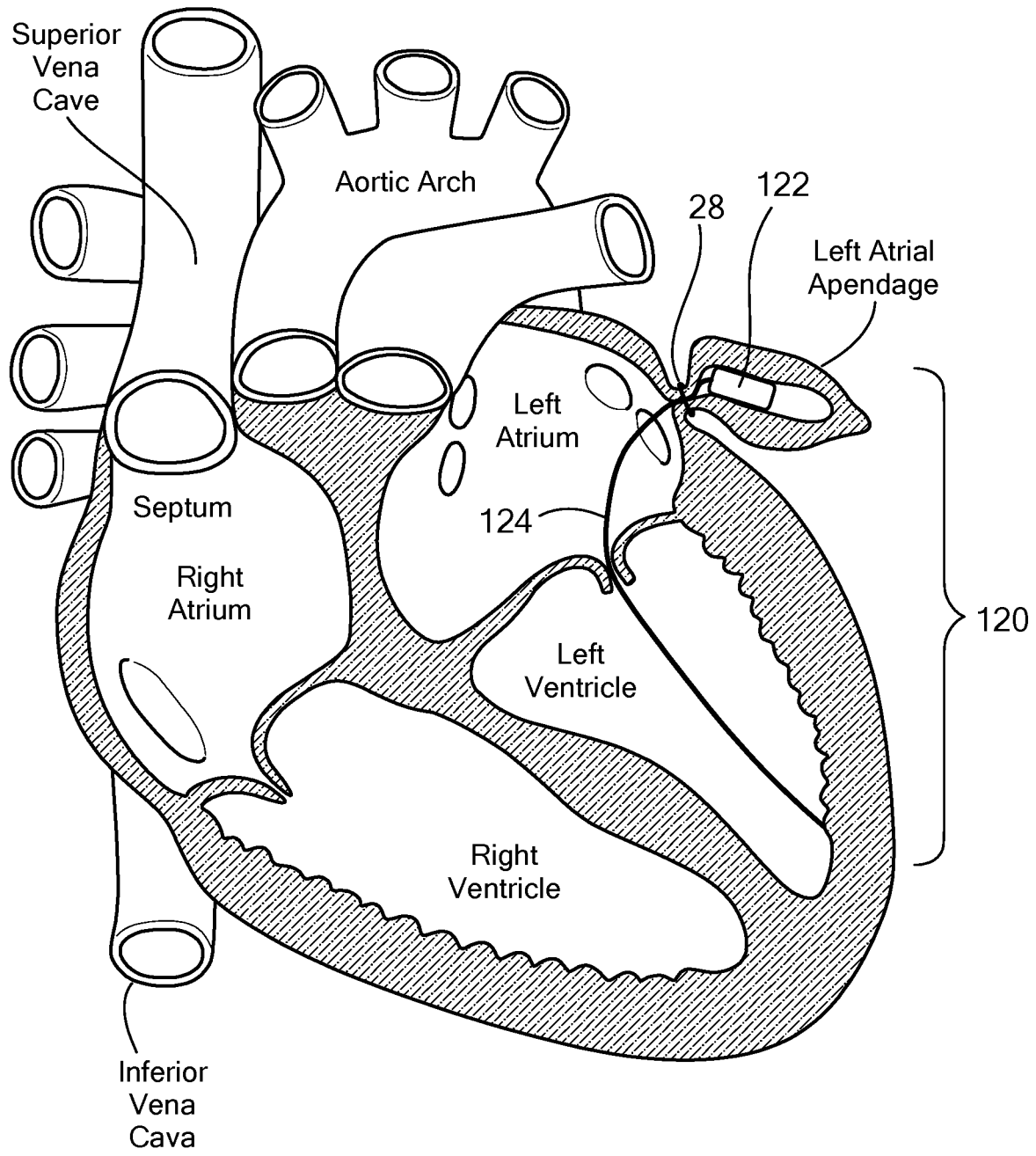
FIGS. 8A-8C show exemplary placements of an implantable pacing device within the LAA.
Figure 8B:
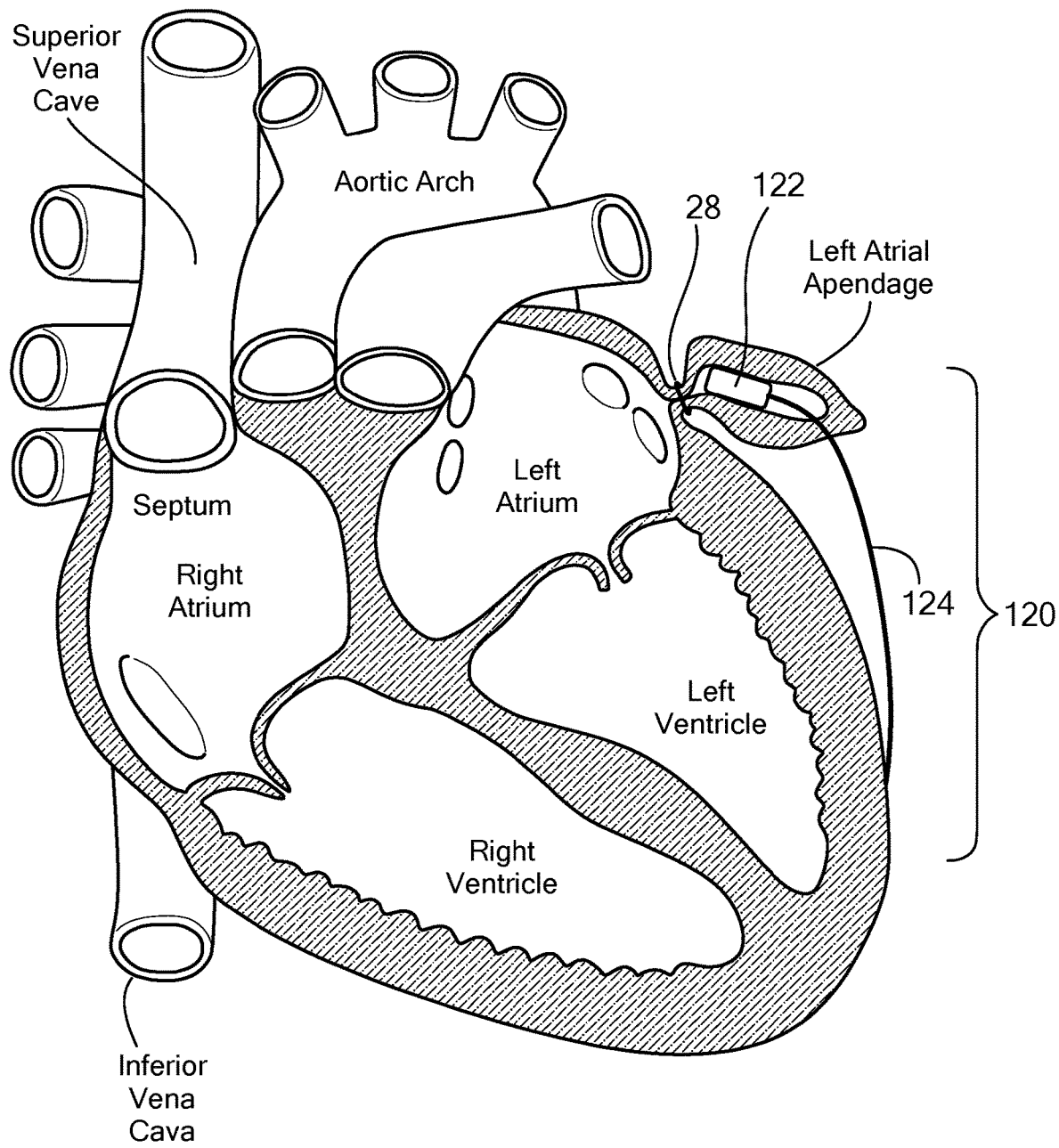

Referring now to FIGS. 8A and 8B, exemplary placements of an implantable pacing device within the LAA are shown. The implantable pacing device 120 may generally include a body 122 and a lead 124. The implantable pacing device 120 may operate from power provided by a battery located within the body 122 and may be sized to be implanted within the LAA. For example, the MICRA® device (Medtronic plc, Dublin, Ireland). Depending on the desired pacing location, the lead 124 may extend from the implantable pacing device 120 within the LAA to an endocardial surface or an epicardial surface of, for example, the left ventricle. Regardless of the location of the lead 124, however, the implantable pacing device 120 may be inserted into the LAA through epicardial access.

As shown in FIG. 8A, the implantable pacing device 120 may be implanted within the LAA and the lead 124 may extend through the ostium into the left atrium, through the mitral valve, and into the left ventricle. In this configuration, the lead 124 may be positioned to pace left ventricle endocardial tissue. As shown in FIG. 8B, the implantable pacing device 120 may be implanted within the LAA and the lead 124 may exit through the LAA tissue. The lead 124 may extend to be in contact with, and configured to pace left ventricle epicardial tissue. However, it will be understood that the lead 124 may be in contact with any area of endocardial or epicardial tissue, depending on the target pacing site.

Figure 8C:
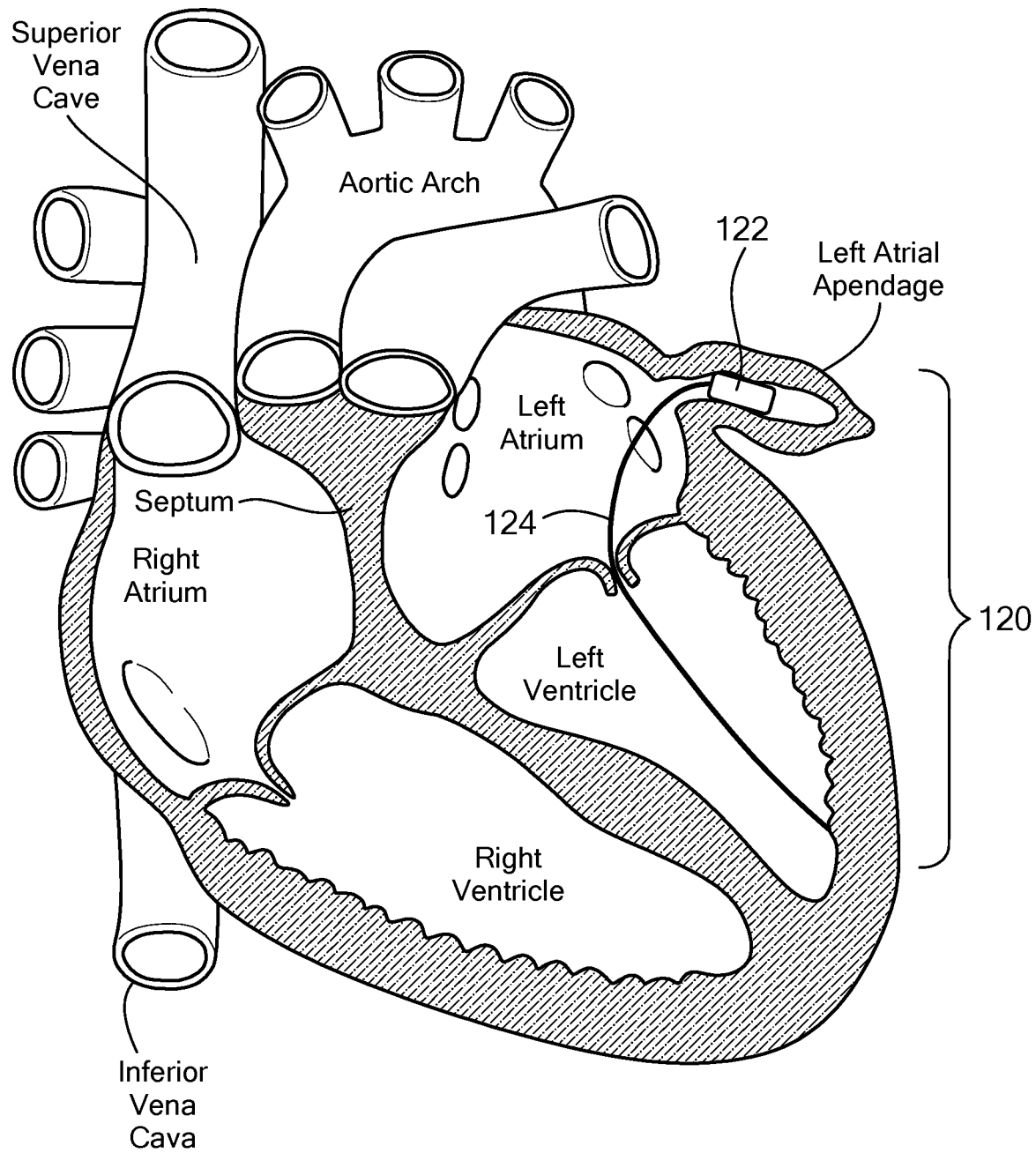

With the implantable pacing device 120 implanted within the LAA, a snare 16/106 and suture 28 may be positioned around the base of the LAA. The snare 16/106 may be used to ablate the ligation location, as discussed herein. The suture 28 may be tightened around the base of the LAA, sealing the LAA with the implantable pacing device 120 inside. Alternatively, the implantable pacing device 120 may be implanted with the LAA without the LAA being ligated by the suture (as shown in FIG. 8C). In this configuration, the implantable pacing device 120 itself may occlude the LAA and provide generally the same effect as ligation with the suture. As a non-limiting example, the implantable pacing device 120 may include a plurality of tines (not shown) that engage with the inner LAA tissue, thereby anchoring the implantable pacing device 120 within the LAA.

It will be understood that the methods described herein may be performed using a ligation device that is capable of ablating tissue through radiofrequency ablation and/or cryoablation, or additionally or alternatively through ultrasound ablation, microwave ablation, electroporation, or the like. Further, it will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for ligating a left atrial appendage, the system including:
   a ligation device including:
      a snare having an elongate body having a proximal portion and a thermally transmissive distal portion, the thermally transmissive distal portion having a first lasso-shaped configuration defining a first diameter; and
      a suture having an elongate body having a proximal portion and a distal portion, the distal portion having a second lasso-shaped configuration defining a second diameter;
      a first slidable element on the thermally transmissive distal portion of the snare, the first slidable element being movable along the snare so that the first diameter is adjustable, wherein the second lasso-shaped configuration is positioned distal of the first slidable element, and within the first lasso-shaped configuration; and
   a console in at least one of electrical communication and fluid communication with the thermally transmissive distal portion of the snare;
   wherein a portion of the suture passes through the first slidable element.

2. The system of claim 1, wherein each of the first diameter and the second diameter are independently adjustable within a range of a plurality of diameters.

3. The system of claim 2, wherein the range of the plurality of diameters includes a diameter sized to allow the left atrial appendage to pass therethrough and a diameter sized to ligate the left atrial appendage.

4. The system of claim 1, wherein the console includes a radiofrequency energy generator, the thermally transmissive distal portion of the snare being configured to transmit radiofrequency energy from the radiofrequency energy generator to the left atrial appendage.

5. The system of claim 4, wherein the proximal portion of the snare is in electrical communication with the radiofrequency energy generator.

6. The system of claim 1, wherein the console includes a refrigerant source, the thermally transmissive distal portion defining a fluid lumen therein that is in fluid communication with the refrigerant source.

7. The system of claim 1, wherein the distal portion of the suture is detachably coupled to the thermally transmissive distal portion of the snare.

8. The system of claim 1, wherein the snare and the suture are composed of a wire or filament of material.

9. The system of claim 1, wherein the distal portion of the snare is of composed of at least one metal wire and the distal portion of the suture is composed of a plastic or non-conductive polymer.

10. The system of claim 1, the ligation device further including:
    an inner sheath surrounding at least a portion of the snare elongate body and the suture elongate body; and
    an outer sheath surrounding at least a portion of the inner sheath, the inner sheath being slidable relative to the snare, the suture, and the outer sheath.

11. The system of claim 10, further comprising a second slidable element on the distal portion of the suture, the second slidable element being movable along the suture so that the second diameter is adjustable, wherein the second slidable element is disposed distal of the first slidable element.

12. The system of claim 11, wherein the advancement of the inner sheath against the first slidable element and the second slidable element moves the first slidable element along the snare and the second slidable element along the suture.

13. The system of claim 1, further comprising a cutting element configured to sever the second lasso-shaped portion from a rest of the suture.

14. The system of claim 1, wherein the second lasso-shaped configuration is configured to remain distal of the first slidable element, and within the first lasso-shaped configuration, while the first lasso-shaped configuration and the second lass-shaped configuration are tightened about the left atrial appendage.

15. A system for ligating a left atrial appendage, the system including: a ligation device including:
- a snare having an elongate body having a proximal portion and a thermally transmissive distal portion, the thermally transmissive distal portion having a first lasso-shaped configuration defining a first diameter; and
- a suture having an elongate body having a proximal portion and a distal portion, the distal portion having a second lasso-shaped configuration defining a second diameter,
- an inner sheath surrounding at least a portion of the snare elongate body and the suture elongate body;
- an outer sheath surrounding at least a portion of the inner sheath, the inner sheath being slidable relative to the snare, the suture, and the outer sheath;
- a first slidable element on the thermally transmissive distal portion of the snare, the first slidable element being movable along the snare so that the first diameter is adjustable, and advancement of the inner sheath against the first slidable element moves the first slidable element along the snare; and
- a second slidable element on the distal portion of the suture, the second slidable element being movable along the suture so that the second diameter is adjustable, and advancement of the inner sheath against the second slidable element moves the second slidable element along the suture, wherein the second slidable element is disposed distal of the first slidable element, and within the first lasso-shaped configuration, and wherein a portion of the suture passes through the first slidable element, and
- a console in at least one of electrical communication and fluid communication with the thermally transmissive distal portion of the snare.

16. The system of claim 15, wherein the distal portion of the suture is detachably coupled to the thermally transmissive distal portion of the snare.

17. The system of claim 15, wherein each of the first diameter and the second diameter are independently adjustable within a range of a plurality of diameters.

18. The system of claim 15, wherein the console includes a radiofrequency energy generator, the thermally transmissive distal portion of the snare being configured to transmit radiofrequency energy from the radiofrequency energy generator to the left atrial appendage.

* * * * *